United States Patent [19]

Ito

[11] 4,247,176
[45] Jan. 27, 1981

[54] OPTICAL SYSTEM FOR EYE FUNDUS INSPECTION APPARATUS

[75] Inventor: Yuji Ito, Chigasaki, Japan

[73] Assignee: Canon Kabushiki Kaisha, Tokyo, Japan

[21] Appl. No.: 931,254

[22] Filed: Aug. 4, 1978

[30] Foreign Application Priority Data

Aug. 9, 1977 [JP] Japan .................................. 52/95359

[51] Int. Cl.³ .......................... A61B 3/14; G03B 29/00
[52] U.S. Cl. ............................................ 351/7; 354/62
[58] Field of Search ......................... 351/7, 13, 14, 16; 354/62

[56] References Cited

U.S. PATENT DOCUMENTS

| | | | |
|---|---|---|---|
| 3,594,071 | 7/1971 | Okajima | 351/7 |
| 3,914,032 | 10/1975 | Takano et al. | 351/7 |
| 3,925,793 | 12/1975 | Matsumura et al. | 351/7 |
| 4,102,563 | 7/1978 | Matsumura et al. | 351/7 |

*Primary Examiner*—John K. Corbin
*Assistant Examiner*—Rodney B. Bovernick
*Attorney, Agent, or Firm*—Toren, McGeady and Stanger

[57] ABSTRACT

In the apparatus disclosed a photographic system is composed of an objective lens and an image forming lens. An illumination system has a part of its light path in common with the photographic system. In the latter the photographic picture angle is adjusted by mounting an attachment lens in front of the objective lens or exchanging the front component lens of the objective lens for an attachment lens. In the illuminating system a masking plate forms a shadow on the pupil of the eye and has a transparent domain. The masking plate is exchanged for another one with a different size of transparent domain when mounting and exchanging the attachment lens. By forming the attachment lens as a positive aplanatic lens or a negative aplanatic lens various aberrations taking place in the illumination light beam and the photographing light beam are compensated. Further, one of the aplanatic points of the aplanatic lens corresponds to the image of the masking plate.

14 Claims, 12 Drawing Figures

OPTICAL SYSTEM FOR EYE FUNDUS INSPECTION APPARATUS

BACKGROUND OF THE INVENTION

The present invention relates to an apparatus for inspecting or photographing an eye fundus, and particularly to an optical system whose inspection or photographic picture angle is variable.

When the dimension of the photographic area, for example the picture size of the film of an eye fundus camera, varied, the photographic magnification is varied accordingly. Consequently, a picture with higher magnification is advantageous when a local part must be inspected clearly, while the picture with lower magnification is suitable when a wide area of the eye fundus is to be photographed.

The standard photographic picture angle for an eye fundus camera is 30°, while the photographic magnification is about 2.3. The photographic picture angle for the so-called wide angle type eye fundus camera is 45°, while the photographic magnification is about 1.8. Consequently, the picture angle of 30° is suitable when a small area is to be inspected in detail, while the 45° angle or more is suitable when a large area is to be inspected so as to confirm a symptom, for example, during an overall inspection.

SUMMARY OF THE INVENTION

A purpose of the present invention is to offer a variable inspecting or photographic picture angle.

Another purpose of the present invention is to offer a means for keeping the size of the image of the masking dot as well as the circular aperture formed between the crystalline lens and the vertex of the cornea be constant despite the variation of the picture angle.

Another purpose of the present invention is to offer a means for decreasing the spherical aberration and the coma occuring when the illumination light beam passes through the objective lens as well as the aberrations occuring when the object light beam reflected on the eye fundus passes through the objective lens.

Another purpose of the present invention is to offer a means for preventing the illumination beam reflected on the attachment lens surface from being mixed into the photographic beam when the attachment lens is attached to the objective lens or a part of the component lenses of the objective lens is exchanged for the attachment lens. The photographic light beam is designated as the one being reflected from the eye fundus and reaching the film.

BRIEF DESCRIPTION OF THE DRAWINGS

FIG. 2A shows an embodiment of the invention.

DESCRIPTION OF PREFERRED EMBODIMENT

Figure 1:
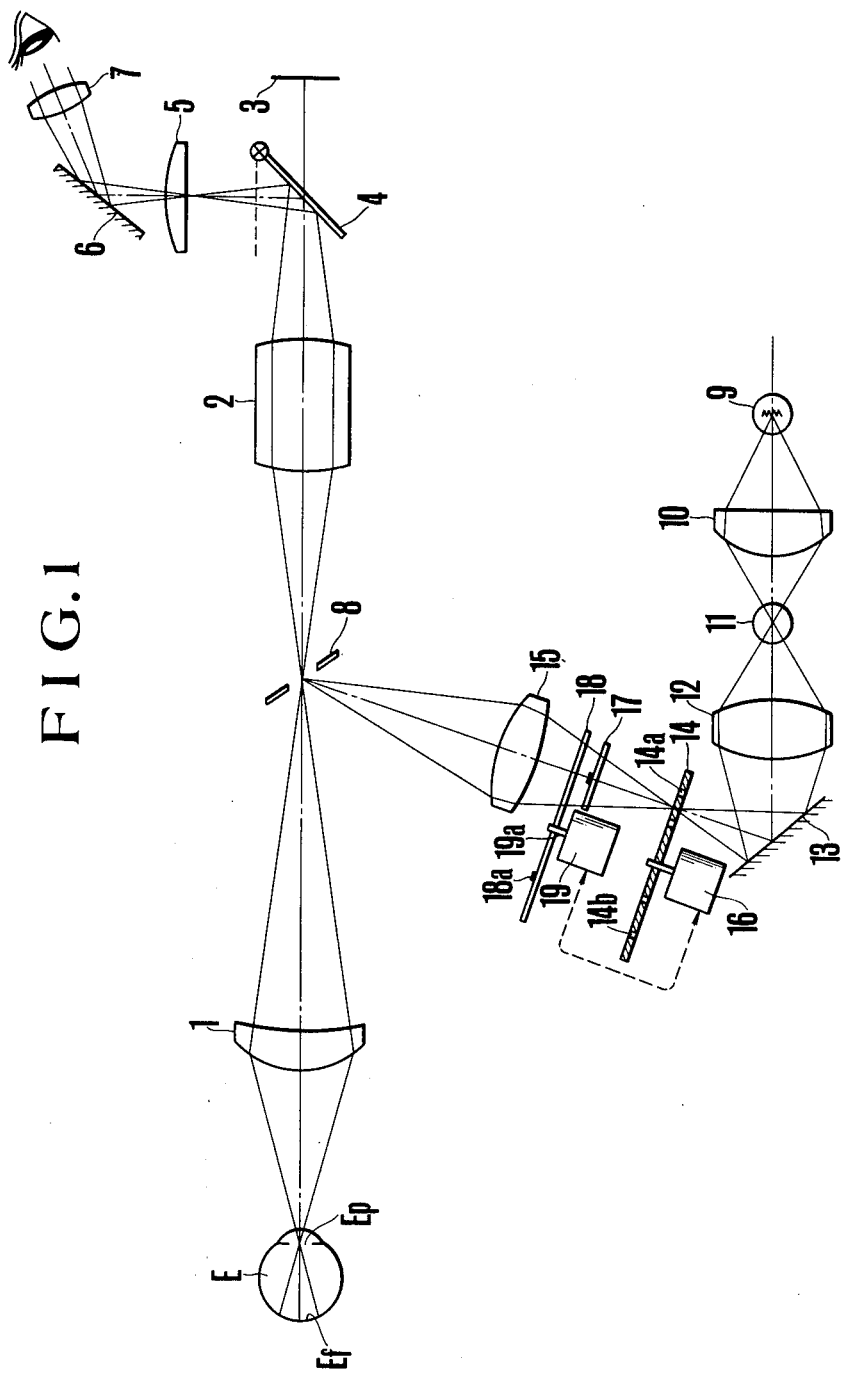
FIG. 1 shows an embodiment of the present invention in lengthwise section.
Figure 2:
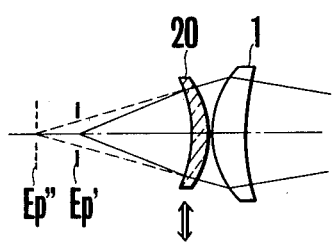
FIG. 2 shows a part of the embodiment with an additional lens in section.
Figure 3:
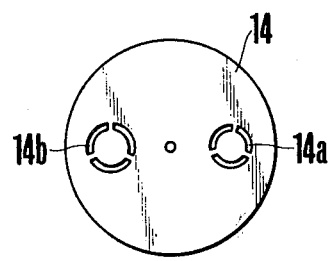
FIG. 3 shows a light shading plate in plane view.
Figure 4:
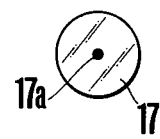
FIG. 4 shows a light shading plate for eliminating the undesirable reflected light in plane view.

The present invention will be explained in detail in accordance with the embodiment shown in FIGS. 1 to 5. FIG. 1 shows an objective lens with picture angle of about 30°, while FIG. 2 shows an objective lens with a picture angle of about 45° provided with an additional lens.

In the drawings, E is the human eye, Ep the pupil and Ef the eye fundus. An objective lens, 1 is composed of a positive meniscus lens and has an aspherical convex surface so as to correct aberrations. The objective lens 1 may be constituted on a bi-convex lens or a plural number of component lenses.

An image forming lens 2 is composed of a plural number of lenses in practice, although shown as one piece of positive lens in the drawing for the sake of simplicity. The lens group 2 projects on a film 3 the intermediate image of the object formed by means of the objective lens 1. A quick return mirror serves to lead the light beam from the object toward the view finder optics. Mirror 4 is provided at an angle to the light path during the observation and is brought out of the light path at the time of photographing. A field lens 5 is arranged at a position almost conjugate with the film 3 with reference to the quick return mirror 4. Reference numeral 6 is the light path deflecting mirror while reference numeral 7 is the eye piece.

A mirror 8 with an opening is provided at an angle in the optical axis arranging the objective lens 1 with the image forming lens 2. Reference numeral 9 represents the light source for observation. Reference numeral 10 represents a first condenser lens, reference numeral 12 represents a second condenser lens and reference numeral 13 represents a light path deflecting mirror. A light shading plate 14 has a plural number of ring-shaped slits, 14a and 14b, as shown in plane view in FIG. 3. These slits serve to form a circular shade and a shade with a circular opening in the front part of the eye, so that the black dot and the aperture stop may be provided separately from each other. In this case, a transparent plate provided with a set of black dots of different sizes and the iris diaphragm with variable aperture are provided.

A relay lens 15 is composed of a plural number of lenses in practice. The light shading plate 14 is conjugate with the mirror 8 with reference to the relay lens 15, while the mirror 8 is arranged conjugate with the pupil Ep of the eye. Thus the illuminating light beam having passed through the slit 14a or 14b is reflected upon the mirror 8 and refracted by the objective lens so as to form an image of the slit on the pupil Ep and thus illuminate the eye fundus Ef evenly.

The aforementioned light shading plate 14 is rotatable around a shaft connected with a driving part 16. Thus, when the driving part 16 is driven, the slit 14a or 14b is selectively set so that the axis of the annular slit corresponds to that of the relay lens group 15. The driving part 16 is driven when an additional lens 20 shown in FIG. 2 is mounted, so that the additional lens should be mounted immediately in front of the objective lens 1 so as to correspond to the optical axis. As explained above, this embodiment is designed such that when the additional lens 20 is mounted, the picture angle is enlarged, so that an aplanatic lens is adopted as positive meniscus lens for the convenient correction of various aberrations. As is shown in FIG. 2, when the additional lens 20 is combined with the original objective lens 1, the distance between the combined lens and the object to be inspected is shortened, so that the position of the pupil of the human eye is shifted to Ep'. Whereby the center of the radius of curvature of the concave surface of the additional lens 20 at the side of the object to be photographed is made to correspond to the center of the pupil Ep', the convex surface at the side of the image is made aplanatic surface and the aplanatic conjugate point Ep" with Ep' is made to correspond to the position (Ep) of the object to be photographed with reference to the original objective lens 1. When the picture angle of the objective optics is enlarged, the size of the image of the ring-shaped slit (14a) projected on the pupil Ep becomes small as compared with the image shown in FIG. 1. Consequently, another slit 14b whose size is enlarged is provided to compensate the change of the magnification. When the additional lens 20 is mounted, the driving part operates so as to set the large sized slit 14b in place.

On the other hand, it is known that in the case of the system in which the illumination passes through the objective lens 1, a part of the light beam is reflected on the lens surface and mixed into the photographing light beam, so as to give inferior influence upon the image. It has already been brought into practice that a black dot is provided on the objective lens surface in order to eliminate the undesirable light reflecting on the lens surface. Also in case of the present invention, it is desirable that on the optical axis between the mirror 8 and the light source a black dot should be provided so as to check the reflection upon the lens surface, because although it is possible to provide black dots on the objective lens 1 and the additional lens 20, the black dot on the objective lens is not profitable in the case of the wide picture angle (Japanese Patent Application Publication No. Sho 44-8406).

Figure 5:
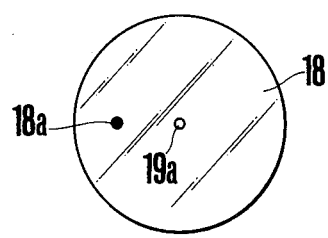
FIG. 5 shows another light shading plate for eliminating the undesirable reflected light in plane view.

A transparent plane plate 17 has a light shading black dot 17a, thus providing a black dot on the optical axis at a position closer to the light source than to the relay lens 15. The light reflected upon the lens surface is thus eliminated. A transparent circular plate, 18 with another black dot 18a as shown in FIG. 5 is connected to a driving part 19. When the driving part 19 runs, the black dot 18a is set on the optical axis. The relation between the black dot 18a and the light reflected upon the additional lens 20 is explained below. Further, this kind of the arrangement has already been proposed with U.S. Patent Application Ser. No. 797,636, now U.S. Pat. No. 4,176,920.

The light which passes through the objective lens 1 reaches the additional lens 20 and is reflected upon its concave surface, out of the light from the image of the circular slit once formed on the mirror 8 with opening returns along the direction, along which the light has come never to reach the film surface, because the light reaches the position diametral to the first reflecting point on the mirror 8 with opening. The reason is that the light returns correctly to the symmetrical position, because the aberrations are effectively eliminated because of its aspherical surface, while the spherical aberration is also eliminated because of an aplanatic surface of the additional lens at the side of the image.

It is possible that the light reflected on the additional lens 20 could pass through the objective lens 1 in a reversed direction so as to reach the opening of the mirror 8. In consequence, when the mirror 8 with opening and the black dot 18 are arranged conjugately with each other with reference to the objective lens 1 and the concave surface of the additional lens 20 at the side of the image, the objective lens 1 and the mirror 8 with opening and the relay lens group 15, while their size is determined in accordance with the magnification of the optical systems then associated, the light reflected on the convex surface of the additional lens 20 at the side of the image never reaches the opening of the mirror 8.

The black dot 18a and the slit 14b are set at the same time, so that it is profitable to operatively engage the driving part 16 with 19 and further with the mounting of the additional lens 20.

The operation of the aforementioned embodiment is explained below. The light beam emitted from the light source 9 is once converged upon a photographic light source 11 by means of the condenser lens 10, then diverged, converged again by means of another condenser lens 12, reflected upon the mirror 13 and condensed on the light shading plate 14. Then, the light beam having passed through the slit 14a of the light shading plate 14, projects the transparent plates 17 and 18 are upon the mirror 8 by means of the relay lens 15. This light beam is then reflected on mirror 8, diverged and again condensed by means of the objective lens 1, so as to form an image of the ring-shaped slit in the neighborhood of pupil Ep and illuminate the eye fundus Ef.

Further, the light beam reflected from the illuminated eye fundus Ef goes out of the eye, is converged by means of the objective lens 1, passes through the opening of the mirror 8 so as to reach the image forming lens group, is reflected by means of the quick return mirror. Thus the image reaches the eye of the inspector through the field lens 5, the mirror 6 and the eye piece 7. When the inspector carries out the release operation, the quick return mirror 4 is brought out of the light path and the photographing light source 11 emits a light so as to expose the film 3 to the light reflected on the eye fundus.

When the additional lens 20 is mounted immediately in front of the objective lens 1 and the driving parts 16 and 19 are operated, another ring-shaped slit 14b is brought into the light path so that the black dot 18a is set on the optical axis. Further, the distance between the objective lens and the object to be photographed is shortened, so that when the apparatus is moved slightly to the eye to be inspected so as to adjust the working distance, and the light source 9 is lit, the inspector can obtain a wider observation through the eye piece lens 7 than before.

The central masking domain of the ring-shaped slit 146 provided in the light shading plate 14 of the aforementioned apparatus to eliminates the illumination light reflected upon the cornea in order to separate the illumination light beam from the photographing light beam. However, in the case of a narrow picture angle, the domain of the shadow made with the above central masking domain covers not only the cornea but also the crystalline lens, so that neither the reflection upon the front and the rear surface of the crystalline lens nor the dispersion brings any problem. On the other hand, in the case of the wide picture angle, the vertical angle of the core mode with the illumination light beam incident on the human eye becomes larger, while the shadow of the above central masking domain becomes shorter, so that the crystalline lens is exposed to the illumination light beam so as to cause a reflection and a dispersion. Consequently, in the case of a wide picture angle of at least 45°, it is desirable to prevent the dispersion as well as the reflection caused with the crystalline lens. The assignee has proposed the eliminating method with the U.S. Patent Application Ser. Nos. 744,809 and 771,738, now U.S. Pat. No. 4,102,563 and U.S. Pat. No. 4,146,310 respectively.

Figure 6:
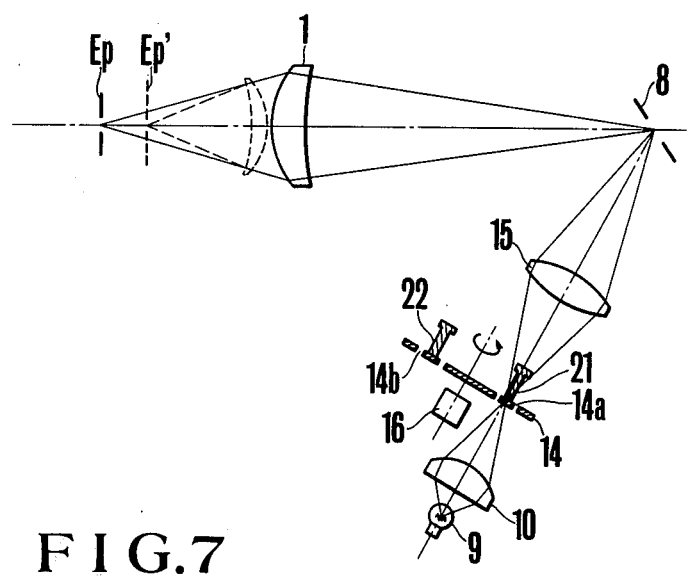
FIG. 6 shows a variation in partial section.
Figure 7:
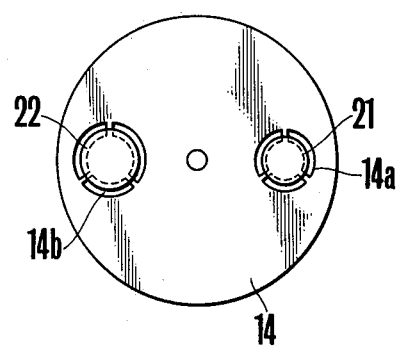
FIG. 7 shows a light shading plate for eliminating the undesirable reflected light in plane view.

FIGS. 6 and 7 show an embodiment of a light shading plate provided with a means for eliminating the dispersion as well as the reflection caused with the crystalline lens. A baffle 21 is secured in the central masking domain of the ring-shaped slit 14a, while another baffle 22 is secured in the central masking domain of the ring-shaped slit 14b. Each of these baffles is composed of a disc with small diameter. A shaft is secured at one end to the center of the disc, and on the other end on the light shading plate so that the image of the disc which is projected by means of the lens group 15 and the objective lens 1 is formed in the neighborhood of the rear surface of the crystalline lens and covers the domain through which the photographic light beam passes. Instead of being supported on a shaft, the baffle can be provided on another transparent plane plate, but it is easier to realize the construction as is shown in FIG. 6.

The diameters of the discs 21 and 22 correspond respectively to the size of the ring-shaped slits 14a and 14b. The apparatus is so designed that the image of the ring-shaped slit formed on the surface of the iris is a little distant from the vertex, so that a part of the cornea is out of the shadow of the central light shading domain. This presents the danger that the illumination light beam could be dispersed. Consequently, it is also advisable that at the back of the light shading plate 14, a baffle is arranged so as to be conjugate with the vertex of the cornea in the same way as in case of the baffle 21 or 22.

In the aforementioned embodiment, slits of various kinds of size are prepared however, it is possible to prepare the relay lens 15 with variable power so that the size of the image of the slit on the mirror 8 should be variable, whereby either the interchangeable relay lenses or a zooming relay lens will do.

Figure 8:
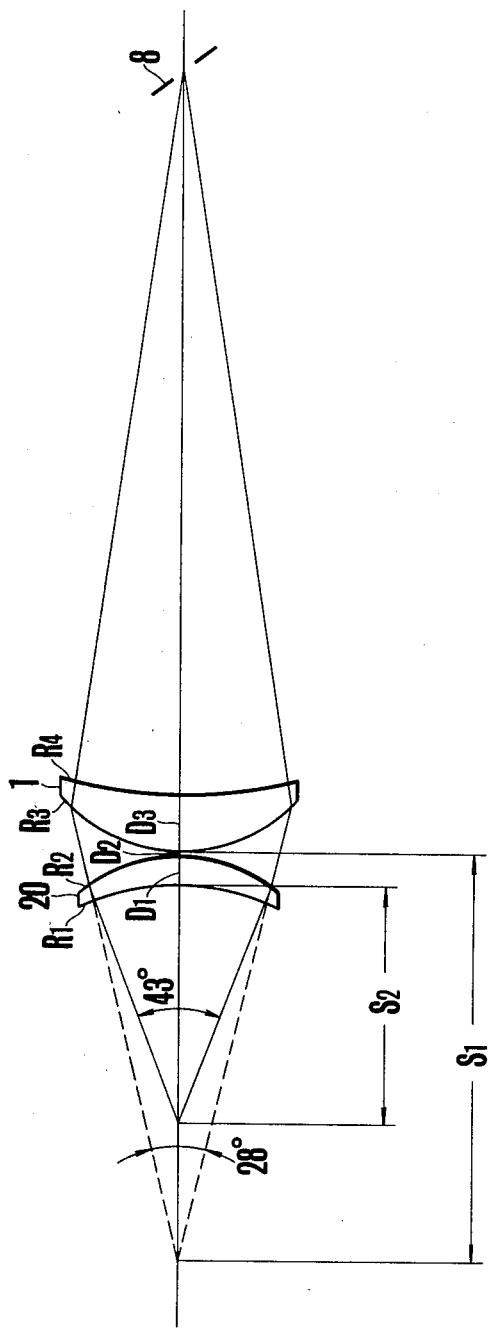
FIG. 8 shows a part of the variation with an additional lens in section.

FIG. 8 shows the objective lens 1 and the attachment 20 for the above embodiment in section. There data are as follows.

| Radius of Curvature | Distance | Refractive factor Nd | Dispersion νd |
| --- | --- | --- | --- |
| R1 = −39.74 | D1 = 4.5 | 1.51633 | 64.1 |
| R2 = −26.66 | D2 = 0.5 | 1. | 0 |
| R3 = 19.85 | D3 = 10.0 | 1.51633 | 64.1 |
| R4 = 120.00 | | | |

(Hereby, the surface R3 is non-spherical).
S1 = 67.09
S2 = 39.74
S1 and S2 are respectively operation distance. S1 is used when only the objective lens 1 is operable and the consequent picture angle is 28°, while S2 is used for the objective lens 1 operate with the attachment lens 20 with the consequent picture angle at 43°.

Further, when the first image of the ring-shaped slit is formed at the position of the mirror 8, the magnification for the secured image at the position of the pupil is $\beta 1 = -0.5$ when the picture angle for the image is 28°. That for the second image of the ring-shaped slit at the position of the pupil is $\beta 2 = -0.33$ when the picture angle for the image is 43°. Consequently, in order to obtain the same size of the image of the ring-shaped slit at the position of the pupil for both of the picture angles, the size of the ring-shaped slit for the picture angle of 43° is to be chosen 1.5 (=0.5/0.33) times as large as that for the picture angle of 28°.

FIGS. 9 (A), (B) and (C) respectively explain the case in which a negative aplanatic lens 30 is used instead of a positive aplanatic lens.

Figure 9A:
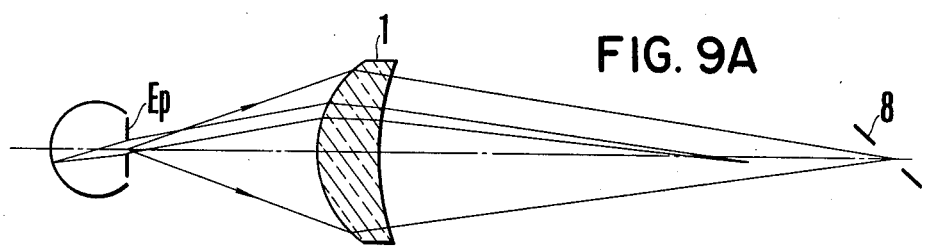
FIGS. 9A, B and C respectively show an objective lens with different picture angle.
Figure 9B:
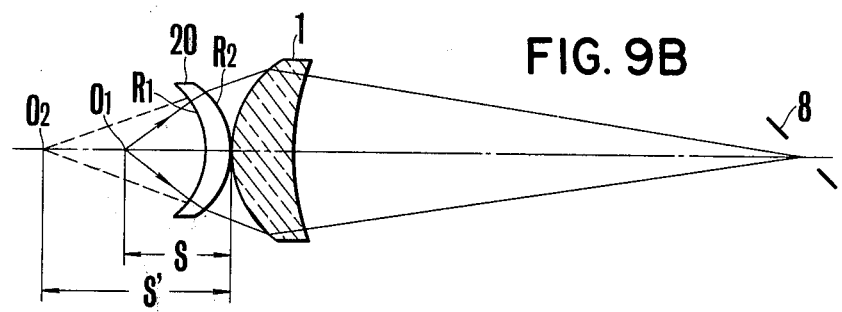

FIG. 9(A) shows the objective lens as standard lens, while FIG. 9(B) shows a positive aplanatic lens 20 provided immediately in front of the objective lens 1. In FIG. 9(B), the center of the radius of curvature of the surface R1 corresponds to O1, while between the aplanatic surface R1 and the aplanatic points O1 and O2, respectively the relations $$S = (1 + 1/n)R2$$

$$S' = (1 + n)R2$$

are satisfied. The refractive factor of the aplanatic lens is represented by n, while the distance between O1 and the vertex of the surface R2 is represented by S the distance between O2 and the vertex of the surface R2 is represented by S'.

Figure 9C:
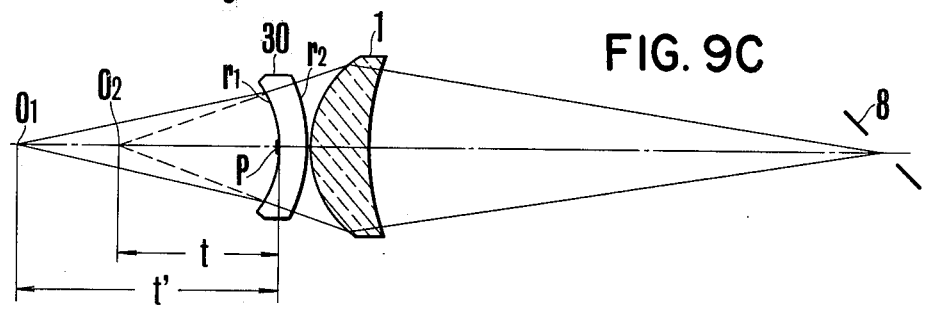

Further, when as shown in FIG. 9(C), a negative aplanatic lens 30 is provided immediately in front of the objective lens 1 or in exchange for a positive aplanatic lens 20, the total picture angle becomes small. In the case of a negative aplanatic lens, the surface R1 at the side of the object is the aplanatic surface. The actual position of the pupil corresponds to O1 out of the aplanatic points O1 and O2 conjugate with each other, while the center of the radius of curvature of the surface R2 corresponds to O2.

Further, supposing that the distance between O1 and the vertex of the surface r1 is t, the distance between O2 and the vertex of the surface t' and the refractive factor of the lens material n', the relations $$t' = (1 + n')r1$$

$$t = (1 + 1/n')r1; \ t' > t$$

are obtained.

Further, on the optical axis of the surface r1 of the aplanatic lens 30, a black dot P is provided so as to eliminate the undesirable reflected light. Although in case of the aforementioned wide angle lens, the black dot is provided in the illumination system lest the picture quality should be inferior, in case of the small angle lens no inconvenience takes place even if the black dot is provided directly on the lens surface. Also in this case, the black dot can be provided in the illumination system as mentioned above. The size of the diaphragm of the light shading plate for eliminating the reflection at the cornea is to be exchanged for a smaller one so as to correspond to the variation of the magnification factor.

What is claimed is:
1. An optical system for an eye fundus inspection apparatus comprising:
objective lens means facing the eye to be inspected;
an image forming lens provided at a position closer to the image than the objective lens;

an illuminating system including at least one beam source, a beam transmitting system and beam reflecting means;

an attachment lens adjacent said objective lens means, said lens being mountable or dismountable, said lens when mounted having an optical axis corresponding to the optical axis of the objective lens means; and masking means between the beam source and the reflecting means for forming a shadow in the eye to eliminate undesirable beam reflections, said masking means being variable in size to keep the size of the shadow formed in the eye to be inspected substantially constant when the attachment lens is mounted and dismounted.

2. An optical system in accordance with claim 1, wherein the beam reflecting means is located between said objective lens means and said image forming lens.

3. An optical system in accordance with claim 1, wherein said objective lens means includes a plurality of component lenses, one of the component lenses being dismounted at the time of mounting the attachment lens.

4. An optical system in accordance with claim 1, wherein the attachment lens is an aplanatic lens, to be mounted on said objective lens means so as to face to the eye to be inspected.

5. An optical system in accordance with claim 1, wherein said beam reflecting means is arranged between said objective lens means and said image forming lens, and wherein shading means for eliminating the light beam reflected on the surface of the attachment lens is dismountably arranged between the light beam source and the light beam reflecting means.

6. An optical system in accordance with claim 1, further comprising beam-intercepting means between the beam source and the reflecting means to eliminate the undesirable beam reflected off the crystalline lens of the eye to be inspected and to keep the size of the shadow formed in the eye to be inspected substantially constant.

7. An optical system for an eye fundus inspection apparatus comprising:
objective lens means facing the eye to be inspected;
an image forming lens provided at a position closer to the image than the objective lens;
an illuminating system including at least one beam source, a beam transmitting system and beam reflecting means;
an attachment lens adjacent said objective lens means, said lens being mountable or dismountable, said lens when mounted having an optical axis corresponding to the optical axis of the objective lens means; and
said masking means including a plurality of annular slits.

8. An optical system for an eye fundus inspection apparatus comprising:
objective lens means facing the eye to be inspected;
an image forming lens provided at a position closer to the image than the objective lens;
an illuminating system including at least one beam source, a beam transmitting system and beam reflecting means;
an attachment lens adjacent said objective lens means, said lens being mountable or dismountable, said lens when mounted having an optical axis corresponding to the optical axis of the objective lens means; and
the masking means including a plurality of slit forming means each forming an annular slit whereby the mounting of one of the slits in the optical path of said illuminating system cooperates with the mounting of said attachment lens.

9. An optical system for an eye fundus inspection apparatus comprising:
an objective lens including convergent lens means and at least one meniscus lens dismountable from and mountable on the objective lens so as to face the eye to be inspected, said meniscus lens having a concave surface facing the eye to be inspected;
an image forming lens to be provided on the image side of said objective lens;
photo-sensitive means at the image side of said image forming lens;
a finder to be optically connected to said image forming lens;
a light beam reflector between said objective lens and said image forming lens;
relay lens means between a light beam source and said light beam reflector;
a mask having a plurality of transparent areas with different sizes; and
setting means connected to said mask so as to mount one of the transparent areas between the beam source and the light beam reflector.

10. An optical system in accordance with claim 9, wherein the mask includes a plurality of shading disks for eliminating undesirable beams due to the crystalline lens.

11. An optical system in accordance with claim 9, wherein the shading means for eliminating undesirable beams reflected on the image side surface of said meniscus lens is mountable and dismountable between said light beam source and said light beam reflector.

12. An optical system in accordance with claim 9, wherein the miniscus lens is an aplanatic lens.

13. An optical system in accordance with claims 4 and 12, wherein the aplanatic lens has a positive power.

14. An optical system in accordance with claims 4 and 12, wherein the aplanatic lens has a negative power.

* * * * *